(12) United States Patent
Zhang et al.

(10) Patent No.: US 8,309,521 B2
(45) Date of Patent: Nov. 13, 2012

(54) SPACER WITH A COATING THEREON FOR USE WITH AN IMPLANT DEVICE

(75) Inventors: Kai Zhang, Warsaw, IN (US); Daniel Buehler, Warsaw, IN (US); Hallie E. Brinkerhuff, Winona Lake, IN (US); Michael E. Hawkins, Columbia City, IN (US); Ralf Klabunde, Winterthur (CH)

(73) Assignee: Zimmer, Inc., Warsaw, IN (US)

( * ) Notice: Subject to any disclaimer, the term of this patent is extended or adjusted under 35 U.S.C. 154(b) by 1226 days.

(21) Appl. No.: 11/765,007

(22) Filed: Jun. 19, 2007

(65) Prior Publication Data

US 2008/0317812 A1 Dec. 25, 2008

(51) Int. Cl.
*A61K 38/00* (2006.01)
*A61K 38/18* (2006.01)
*A61B 17/88* (2006.01)
*A61B 17/80* (2006.01)

(52) U.S. Cl. ........ 514/16.7; 514/8.8; 606/281; 606/280; 606/70; 606/71

(58) Field of Classification Search .................. None
See application file for complete search history.

(56) References Cited

U.S. PATENT DOCUMENTS

| | | |
|---|---|---|
| 3,605,123 A | 9/1971 | Hahn |
| 3,643,658 A | 2/1972 | Steinemenan |
| 4,004,064 A | 1/1977 | Kessler |
| 4,338,926 A * | 7/1982 | Kummer et al. ............. 606/70 |
| 4,563,489 A | 1/1986 | Urist |
| 4,570,271 A | 2/1986 | Sump |
| 4,713,076 A | 12/1987 | Draenert |
| 4,923,471 A | 5/1990 | Morgan |
| 4,943,292 A * | 7/1990 | Foux .......................... 606/70 |
| 5,084,050 A | 1/1992 | Draenert |
| 5,198,308 A | 3/1993 | Shetty |
| 5,282,861 A | 2/1994 | Kaplan |
| 5,302,414 A | 4/1994 | Alkhimov |
| 5,323,954 A | 6/1994 | Shetty |
| 5,383,934 A | 1/1995 | Armini |
| 5,397,796 A | 3/1995 | Zoller et al. |
| 5,447,724 A | 9/1995 | Helmus et al. |
| 5,458,653 A | 10/1995 | Davidson |
| 5,470,829 A | 11/1995 | Prisell et al. |
| 5,492,697 A | 2/1996 | Boyan et al. |
| 5,529,914 A | 6/1996 | Hubbell et al. |
| 5,534,524 A | 7/1996 | Bonewald et al. |
| 5,535,810 A | 7/1996 | Compton |
| 5,543,441 A | 8/1996 | Rhee et al. |
| 5,550,178 A | 8/1996 | Desai et al. |
| 5,554,594 A | 9/1996 | Zoller et al. |
| 5,565,407 A | 10/1996 | Southard |
| 5,569,463 A | 10/1996 | Helmus et al. |
| 5,573,934 A | 11/1996 | Hubbell et al. |
| 5,631,011 A | 5/1997 | Wadstrom |
| 5,658,334 A | 8/1997 | Caldarise |
| 5,658,935 A | 8/1997 | Klingler et al. |
| 5,665,118 A | 9/1997 | LaSalle |
| 5,688,855 A | 11/1997 | Stoy et al. |
| 5,713,410 A | 2/1998 | LaSalle |
| 5,736,160 A | 4/1998 | Ringeisen et al. |
| 5,788,979 A | 8/1998 | Alt et al. |
| 5,801,033 A | 9/1998 | Hubbell et al. |
| 5,824,651 A | 10/1998 | Nanci et al. |
| 5,834,274 A | 11/1998 | Hubbell et al. |
| 5,843,743 A | 12/1998 | Hubbell et al. |
| 5,866,113 A | 2/1999 | Hendriks et al. |
| 5,893,846 A | 4/1999 | Bales |
| 5,925,553 A | 7/1999 | Clark et al. |
| 5,928,916 A | 7/1999 | Keogh |
| 5,932,299 A | 8/1999 | Katoot |
| 5,947,893 A | 9/1999 | Agrawal et al. |
| 6,004,943 A | 12/1999 | Shi et al. |
| 6,099,562 A | 8/2000 | Ding et al. |
| 6,120,536 A | 9/2000 | Ding et al. |
| 6,121,027 A | 9/2000 | Clapper et al. |
| 6,153,252 A | 11/2000 | Hossainy et al. |
| 6,166,173 A | 12/2000 | Mao et al. |
| 6,177,095 B1 | 1/2001 | Sawhney et al. |
| 6,179,817 B1 | 1/2001 | Zhong |

(Continued)

FOREIGN PATENT DOCUMENTS

CH 657519 9/1986

(Continued)

OTHER PUBLICATIONS

ISR/WO From PCT/US2009/032608. Jegnathian Karthiekeyan. Cold Spray Technology, Mar. 2005, pp. 33-35, ASB Industries, Barberton, OH.
ISR/WO From PCT/US2009/031502.
Uhthoff, Hans K. et al. Journal of Orthopaedic Science, Internal Plate Fixation of Fractures: Short History and Recent Developments, 11:118-126, (2006). The Japanese Orthopaedic Association, Japan.
Aleksyniene, Ramune et al. Medicina (Kaunas), Parathyroid Hormone—Possible Future Drug for Orthopedic Surgery; vol. 40(9): 842-849 (2004).
Termaat, M.F. et al. The Journal of Bone & Joint Surgery, Bone Morphogenetic Proteins. Development and Clinical Efficacy in the Treatment of Fractures and Bone Defects, 87-A (6): 1366-1378 (Jun. 2005).
Morris, Carol D. et al. The Journal of Bone & Joint Surgery, Bisphosphonates in Orthopaedic Surgery, 87-A (7): 1608-1618 (Jul. 2005).
Pavoor, Prem V. et al. Biomaterials, Wear Reduction of Orthopaedic Bearing Surfaces Using Polyelectrolyte Multilayer Nanocoatings, 27: 1527-1533 (2006).
International Search Report of Application No. 08252074.2 search completed on Sep. 29, 2008.
"European Application Serial No. EP08252074, European Search Report mailed Sep. 29, 2008", 2 pgs.

(Continued)

*Primary Examiner* — Xiaozhen Xie
(74) *Attorney, Agent, or Firm* — Schwegman, Lundberg & Woessner, P.A.

(57) ABSTRACT

The present invention relates to a spacer, such as a polymeric spacer, for use with an implant device, e.g., a bone plate, for splinting a fracture of a bone. The spacer includes a body defining a bone healing surface, wherein at least a portion of the bone healing surface has a coating which includes a therapeutic agent, a polymeric carrier, and a buffer medium to stimulate bone growth and/or promote fracture healing. A kit is also disclosed which includes one or more of the spacers, at least one bone plate, and optionally one or more bone screws for securing the bone plate to bone. A method for promoting fracture healing in bone is further disclosed which includes securely situating a coated portion of the spacer adjacent bone.

17 Claims, 1 Drawing Sheet

U.S. PATENT DOCUMENTS

| | | |
|---|---|---|
| 6,197,051 B1 | 3/2001 | Zhong |
| 6,238,687 B1 | 5/2001 | Mao et al. |
| 6,254,634 B1 | 7/2001 | Anderson et al. |
| 6,258,121 B1 | 7/2001 | Yang et al. |
| 6,284,305 B1 | 9/2001 | Ding et al. |
| 6,309,660 B1 | 10/2001 | Hsu et al. |
| 6,313,119 B1 | 11/2001 | Peyman et al. |
| 6,316,522 B1 | 11/2001 | Loomis et al. |
| 6,322,797 B1 | 11/2001 | Mao et al. |
| 6,368,658 B1 | 4/2002 | Schwarz et al. |
| 6,395,023 B1 | 5/2002 | Summers |
| 6,395,029 B1 | 5/2002 | Levy |
| 6,451,373 B1 | 9/2002 | Hossainy et al. |
| 6,455,541 B1 | 9/2002 | Bonewald et al. |
| 6,461,631 B1 | 10/2002 | Dunn et al. |
| 6,486,232 B1 | 11/2002 | Wise et al. |
| 6,492,356 B1 | 12/2002 | Peyman et al. |
| 6,500,481 B1 | 12/2002 | Vanderlaan et al. |
| 6,506,437 B1 | 1/2003 | Harish et al. |
| 6,514,515 B1 | 2/2003 | Williams |
| 6,514,734 B1 | 2/2003 | Clapper et al. |
| 6,528,080 B2 | 3/2003 | Dunn et al. |
| 6,540,746 B1 | 4/2003 | Buhler et al. |
| 6,545,097 B2 | 4/2003 | Pinchuk et al. |
| 6,558,734 B2 | 5/2003 | Koulik et al. |
| 6,596,402 B2 | 7/2003 | Soerens et al. |
| 6,600,010 B2 | 7/2003 | Mao et al. |
| 6,620,194 B2 | 9/2003 | Ding et al. |
| 6,632,446 B1 | 10/2003 | Hubbell et al. |
| 6,656,517 B2 | 12/2003 | Michal et al. |
| 6,669,980 B2 | 12/2003 | Hansen |
| 6,673,385 B1 | 1/2004 | Ding et al. |
| 6,692,498 B1 * | 2/2004 | Niiranen et al. ................ 606/70 |
| 6,692,790 B2 | 2/2004 | Liu et al. |
| 6,723,350 B2 | 4/2004 | Burrell et al. |
| 6,730,324 B2 | 5/2004 | Troczynski et al. |
| 6,733,768 B2 | 5/2004 | Hossainy et al. |
| 6,743,521 B2 | 6/2004 | Hubbell et al. |
| 6,746,685 B2 | 6/2004 | Williams |
| 6,749,639 B2 | 6/2004 | Lewallen |
| 6,833,192 B1 | 12/2004 | Caruso et al. |
| 6,833,363 B2 | 12/2004 | Renier et al. |
| 6,855,329 B1 | 2/2005 | Shakesheff et al. |
| 6,866,860 B2 | 3/2005 | Nathan |
| 6,869,445 B1 | 3/2005 | Johnson |
| 6,872,799 B2 | 3/2005 | Nathan |
| 6,881,766 B2 | 4/2005 | Hain |
| 6,899,107 B2 | 5/2005 | Lewandrowski et al. |
| 6,899,731 B2 | 5/2005 | Li et al. |
| 6,921,811 B2 | 7/2005 | Zamora et al. |
| 6,923,986 B2 | 8/2005 | Pathak et al. |
| 6,923,996 B2 | 8/2005 | Epstein et al. |
| 6,945,448 B2 | 9/2005 | Medlin |
| 6,946,443 B2 | 9/2005 | Blanchat et al. |
| 6,967,234 B2 | 11/2005 | Nathan |
| 6,969,400 B2 | 11/2005 | Rhee et al. |
| 6,986,899 B2 | 1/2006 | Hossainy et al. |
| 6,991,681 B2 | 1/2006 | Yoe |
| 6,991,802 B1 | 1/2006 | Ahola et al. |
| 6,994,883 B2 | 2/2006 | Layrolle et al. |
| 6,998,134 B2 | 2/2006 | Schmidmaier et al. |
| 7,001,421 B2 | 2/2006 | Cheng et al. |
| 7,008,979 B2 | 3/2006 | Schottman et al. |
| 7,112,361 B2 | 9/2006 | Lynn et al. |
| 7,148,209 B2 | 12/2006 | Hoemann et al. |
| 7,157,096 B2 | 1/2007 | Zhang et al. |
| 7,163,715 B1 | 1/2007 | Kramer |
| 7,185,695 B1 | 3/2007 | Santeler |
| 7,186,811 B2 | 3/2007 | Lindholm et al. |
| 2002/0018798 A1 | 2/2002 | Sewing et al. |
| 2002/0041899 A1 | 4/2002 | Chudzik et al. |
| 2002/0082552 A1 | 6/2002 | Ding et al. |
| 2002/0084194 A1 | 7/2002 | Redepenning |
| 2002/0087184 A1 | 7/2002 | Eder et al. |
| 2002/0103526 A1 | 8/2002 | Steinke |
| 2002/0111590 A1 | 8/2002 | Davila et al. |
| 2002/0119179 A1 | 8/2002 | Rezania et al. |
| 2002/0120333 A1 | 8/2002 | Keogh et al. |
| 2002/0131989 A1 | 9/2002 | Brown et al. |
| 2002/0151617 A1 | 10/2002 | Mao et al. |
| 2002/0165608 A1 | 11/2002 | Llanos et al. |
| 2002/0192182 A1 | 12/2002 | Massia et al. |
| 2003/0004568 A1 | 1/2003 | Ken et al. |
| 2003/0007991 A1 | 1/2003 | Masters |
| 2003/0083740 A1 | 5/2003 | Pathak |
| 2003/0088307 A1 | 5/2003 | Shulze et al. |
| 2003/0099762 A1 | 5/2003 | Zhang et al. |
| 2003/0113478 A1 | 6/2003 | Dang et al. |
| 2003/0114937 A1 | 6/2003 | Leatherbury et al. |
| 2003/0117579 A1 | 6/2003 | Morris et al. |
| 2003/0118692 A1 | 6/2003 | Wang et al. |
| 2003/0124172 A1 | 7/2003 | Lopez Lacomba et al. |
| 2003/0124368 A1 | 7/2003 | Lynn et al. |
| 2003/0129130 A1 | 7/2003 | Guire et al. |
| 2003/0157030 A1 | 8/2003 | Davis et al. |
| 2003/0185752 A1 | 10/2003 | Nathan et al. |
| 2003/0219562 A1 | 11/2003 | Rypacek et al. |
| 2003/0228364 A1 | 12/2003 | Nathan |
| 2003/0229393 A1 | 12/2003 | Kutryk et al. |
| 2004/0022853 A1 * | 2/2004 | Ashton et al. ................ 424/468 |
| 2004/0033249 A1 | 2/2004 | Sewing et al. |
| 2004/0039441 A1 | 2/2004 | Rowland et al. |
| 2004/0044404 A1 | 3/2004 | Stucke et al. |
| 2004/0049265 A1 | 3/2004 | Ding et al. |
| 2004/0051201 A1 | 3/2004 | Greenhalgh et al. |
| 2004/0063654 A1 | 4/2004 | Davis et al. |
| 2004/0081745 A1 | 4/2004 | Hansen |
| 2004/0086493 A1 | 5/2004 | Hubbell et al. |
| 2004/0086543 A1 | 5/2004 | Keogh et al. |
| 2004/0091462 A1 | 5/2004 | Lin et al. |
| 2004/0091603 A1 | 5/2004 | Priewe |
| 2004/0093080 A1 | 5/2004 | Helmus et al. |
| 2004/0106985 A1 | 6/2004 | Jang |
| 2004/0109892 A1 | 6/2004 | Shalaby |
| 2004/0117007 A1 | 6/2004 | Whitbourne et al. |
| 2004/0120982 A1 | 6/2004 | Diana et al. |
| 2004/0126405 A1 | 7/2004 | Sahatjian et al. |
| 2004/0133271 A1 | 7/2004 | Jang |
| 2004/0137066 A1 | 7/2004 | Jayaraman |
| 2004/0138695 A1 | 7/2004 | Li et al. |
| 2004/0147999 A1 | 7/2004 | Udipi et al. |
| 2004/0157073 A1 | 8/2004 | Burrell et al. |
| 2004/0170752 A1 | 9/2004 | Luthra et al. |
| 2004/0172121 A1 | 9/2004 | Eidenschink et al. |
| 2004/0185086 A1 | 9/2004 | Massia et al. |
| 2004/0215313 A1 | 10/2004 | Cheng |
| 2004/0215336 A1 | 10/2004 | Udipi et al. |
| 2004/0241202 A1 | 12/2004 | Chluba et al. |
| 2004/0241234 A1 | 12/2004 | Vilkov |
| 2005/0025752 A1 | 2/2005 | Kutryk et al. |
| 2005/0025799 A1 | 2/2005 | Hossainy et al. |
| 2005/0031689 A1 | 2/2005 | Shults et al. |
| 2005/0031793 A1 | 2/2005 | Moeller et al. |
| 2005/0036946 A1 | 2/2005 | Pathak et al. |
| 2005/0048121 A1 | 3/2005 | East et al. |
| 2005/0049694 A1 | 3/2005 | Neary |
| 2005/0060028 A1 | 3/2005 | Horres et al. |
| 2005/0079200 A1 | 4/2005 | Rathenow et al. |
| 2005/0084515 A1 | 4/2005 | Udipi et al. |
| 2005/0085605 A1 | 4/2005 | Nathan |
| 2005/0095267 A1 | 5/2005 | Campbell et al. |
| 2005/0101692 A1 | 5/2005 | Sohier et al. |
| 2005/0106204 A1 | 5/2005 | Hossainy et al. |
| 2005/0112170 A1 | 5/2005 | Hossainy et al. |
| 2005/0112172 A1 | 5/2005 | Pacetti |
| 2005/0129731 A1 | 6/2005 | Horres et al. |
| 2005/0142163 A1 * | 6/2005 | Hunter et al. ................ 424/423 |
| 2005/0147647 A1 | 7/2005 | Glauser et al. |
| 2005/0149171 A1 | 7/2005 | McCullagh et al. |
| 2005/0152955 A1 | 7/2005 | Akhave et al. |
| 2005/0153429 A1 | 7/2005 | Liebmann-Vinson et al. |
| 2005/0154442 A1 | 7/2005 | Eidenschink et al. |
| 2005/0154450 A1 | 7/2005 | Larson et al. |
| 2005/0158359 A1 | 7/2005 | Epstein et al. |
| 2005/0165128 A1 | 7/2005 | Cohn et al. |
| 2005/0169882 A1 | 8/2005 | Lowe et al. |
| 2005/0169969 A1 | 8/2005 | Li et al. |

| | | | | | | |
|---|---|---|---|---|---|---|
| 2005/0180919 A1 | 8/2005 | Tedeschi | | 2006/0251824 A1 | 11/2006 | Boulais et al. |
| 2005/0182473 A1 | 8/2005 | Eidenschink et al. | | 2006/0252981 A1 | 11/2006 | Matsuda et al. |
| 2005/0183259 A1 | 8/2005 | Eidenschink et al. | | 2006/0257377 A1 | 11/2006 | Atala et al. |
| 2005/0187376 A1 | 8/2005 | Pacetti | | 2006/0263830 A1 | 11/2006 | Grinstaff et al. |
| 2005/0187602 A1 | 8/2005 | Eidenschink | | 2006/0263831 A1 | 11/2006 | Grinstaff et al. |
| 2005/0187611 A1 | 8/2005 | Ding et al. | | 2006/0264531 A1 | 11/2006 | Zhao |
| 2005/0191333 A1 | 9/2005 | Hsu | | 2006/0286064 A1 | 12/2006 | Turnell et al. |
| 2005/0208093 A1 | 9/2005 | Glauser et al. | | 2006/0286071 A1 | 12/2006 | Epstein et al. |
| 2005/0208100 A1 | 9/2005 | Weber et al. | | 2006/0293406 A1 | 12/2006 | Bennett et al. |
| 2005/0208200 A1 | 9/2005 | Ding et al. | | 2007/0016163 A1 | 1/2007 | Santini, Jr. et al. |
| 2005/0214339 A1 | 9/2005 | Tang et al. | | 2007/0020308 A1 | 1/2007 | Richard et al. |
| 2005/0215722 A1 | 9/2005 | Pinchunk et al. | | 2007/0020469 A1 | 1/2007 | Wood et al. |
| 2005/0220837 A1 | 10/2005 | Disegi et al. | | 2007/0026043 A1 | 2/2007 | Guan et al. |
| 2005/0220839 A1 | 10/2005 | DeWitt et al. | | 2007/0032882 A1 | 2/2007 | Lodhi et al. |
| 2005/0220840 A1 | 10/2005 | DeWitt et al. | | 2007/0037737 A1 | 2/2007 | Hoemann et al. |
| 2005/0220841 A1 | 10/2005 | DeWitt et al. | | 2007/0038300 A1 | 2/2007 | Bao et al. |
| 2005/0220842 A1 | 10/2005 | DeWitt et al. | | 2007/0041952 A1 | 2/2007 | Guilak et al. |
| 2005/0220843 A1 | 10/2005 | DeWitt et al. | | 2007/0042017 A1 | 2/2007 | Kutryk et al. |
| 2005/0244363 A1 | 11/2005 | Hossainy et al. | | 2007/0043374 A1 | 2/2007 | Evans |
| 2005/0244453 A1 | 11/2005 | Stucke et al. | | 2007/0043433 A1 | 2/2007 | Chandrasekaran et al. |
| 2005/0244459 A1 | 11/2005 | DeWitt et al. | | 2007/0045902 A1 | 3/2007 | Brauker et al. |
| 2005/0245637 A1 | 11/2005 | Hossainy et al. | | 2007/0048291 A1 | 3/2007 | Mang et al. |
| 2005/0251250 A1 | 11/2005 | Verhoeven et al. | | 2007/0048292 A1 | 3/2007 | Morita et al. |
| 2005/0255142 A1 | 11/2005 | Chudzik et al. | | 2007/0053963 A1 | 3/2007 | Hotchkiss et al. |
| 2005/0266038 A1 | 12/2005 | Glauser et al. | | 2007/0054127 A1 | 3/2007 | Hergenrother et al. |
| 2005/0266077 A1 | 12/2005 | Royer | | 2007/0055095 A1 | 3/2007 | Chu et al. |
| 2005/0271700 A1 | 12/2005 | DesNoyer et al. | | 2007/0055367 A1 | 3/2007 | Kutryk et al. |
| 2005/0271701 A1 | 12/2005 | Cottone, Jr. et al. | | 2007/0100450 A1 | 5/2007 | Hodorek |
| 2005/0274478 A1 | 12/2005 | Verner | | 2007/0162015 A1 | 7/2007 | Winquist et al. |
| 2005/0283224 A1 | 12/2005 | King | | 2007/0191848 A1 * | 8/2007 | Wack et al. ............ 606/69 |
| 2005/0288229 A1 | 12/2005 | Sindrey et al. | | 2008/0027458 A1 | 1/2008 | Aikins et al. |
| 2006/0003008 A1 | 1/2006 | Gibson et al. | | 2008/0183172 A1 | 7/2008 | Fritzinger |
| 2006/0008500 A1 | 1/2006 | Chavan et al. | | 2008/0234749 A1 | 9/2008 | Forstein |
| 2006/0009839 A1 | 1/2006 | Tan | | 2009/0171398 A1 | 7/2009 | Phillips et al. |
| 2006/0013850 A1 | 1/2006 | Domb | | 2009/0287215 A1 | 11/2009 | Fisher et al. |
| 2006/0018948 A1 | 1/2006 | Guire et al. | | 2009/0312760 A1 | 12/2009 | Forstein et al. |
| 2006/0025848 A1 | 2/2006 | Weber et al. | | | | |
| 2006/0035854 A1 | 2/2006 | Goldstein et al. | | | | |
| 2006/0036311 A1 | 2/2006 | Nakayama et al. | | | | |

FOREIGN PATENT DOCUMENTS

| | | |
|---|---|---|
| DE | 4106971 | 3/1992 |
| EP | 0372662 | 6/1990 |
| EP | 0616814 A1 | 3/1994 |
| EP | 1273303 A1 | 1/2003 |
| EP | 1144018 B1 | 3/2004 |
| EP | 1806155 | 7/2007 |
| WO | WO9307835 | 4/1993 |
| WO | 9628117 | 9/1996 |
| WO | WO9738469 | 10/1997 |
| WO | 0139680 | 6/2001 |
| WO | 0182989 A1 | 11/2001 |
| WO | 03077772 | 9/2003 |
| WO | 2005120203 | 12/2005 |
| WO | WO2007014279 | 2/2007 |
| WO | 2007038559 | 4/2007 |
| WO | WO2007053022 | 5/2007 |

| | | | | | | |
|---|---|---|---|---|---|---|
| 2006/0036316 A1 | 2/2006 | Zeltinger et al. |
| 2006/0039947 A1 | 2/2006 | Schmidmaier et al. |
| 2006/0039950 A1 | 2/2006 | Zhou et al. |
| 2006/0045901 A1 | 3/2006 | Weber |
| 2006/0057277 A1 | 3/2006 | Chappa |
| 2006/0067969 A1 | 3/2006 | Lu et al. |
| 2006/0093646 A1 | 5/2006 | Cima et al. |
| 2006/0105018 A1 | 5/2006 | Epstein et al. |
| 2006/0121081 A1 | 6/2006 | Labrecque et al. |
| 2006/0165754 A1 | 7/2006 | Ranade |
| 2006/0188541 A1 | 8/2006 | Richelsoph et al. |
| 2006/0198868 A1 | 9/2006 | DeWitt et al. |
| 2006/0204536 A1 | 9/2006 | Shults et al. |
| 2006/0204542 A1 | 9/2006 | Zhang et al. |
| 2006/0210598 A1 | 9/2006 | Evans et al. |
| 2006/0210602 A1 | 9/2006 | Sehl et al. |
| 2006/0216772 A1 | 9/2006 | Grinstaff et al. |
| 2006/0222681 A1 | 10/2006 | Richard |
| 2006/0222756 A1 | 10/2006 | Davila et al. |
| 2006/0233801 A1 | 10/2006 | Brunkow et al. |
| 2006/0233841 A1 | 10/2006 | Brodbeck et al. |
| 2006/0233941 A1 | 10/2006 | Olson |
| 2006/0240063 A9 | 10/2006 | Hunter et al. |
| 2006/0246103 A1 | 11/2006 | Ralph et al. |
| 2006/0246105 A1 | 11/2006 | Molz et al. |
| 2006/0246110 A1 | 11/2006 | Brandon et al. |
| 2006/0247793 A1 | 11/2006 | Trieu et al. |

OTHER PUBLICATIONS

"European Application Serial No. EP08252074, Extended European Search Report mailed Oct. 9, 2008", 5 pgs.

"European Application Serial No. EP08252074, Office Action mailed Aug. 7, 2009", 1 pg.

"European Application Serial No. EP08252074, Response filed Feb. 8, 2010 to Office Action mailed Aug. 7, 2009", 16 pgs.

"European Application Serial No. EP08252074, Result of Consultation mailed Apr. 15, 2011", 18 pgs.

* cited by examiner

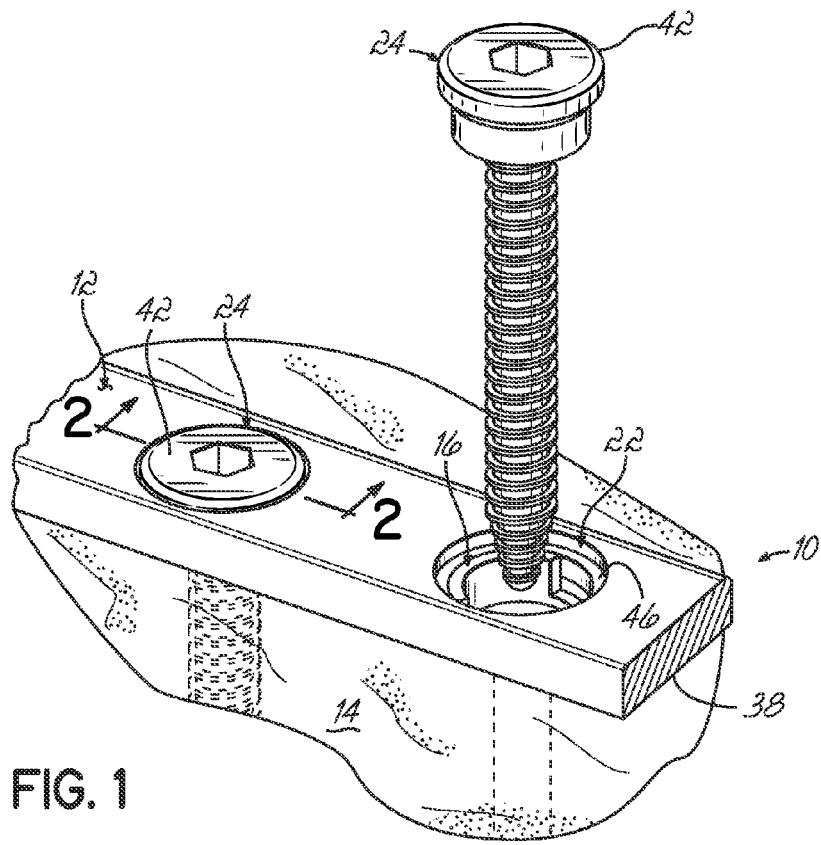
FIG. 1
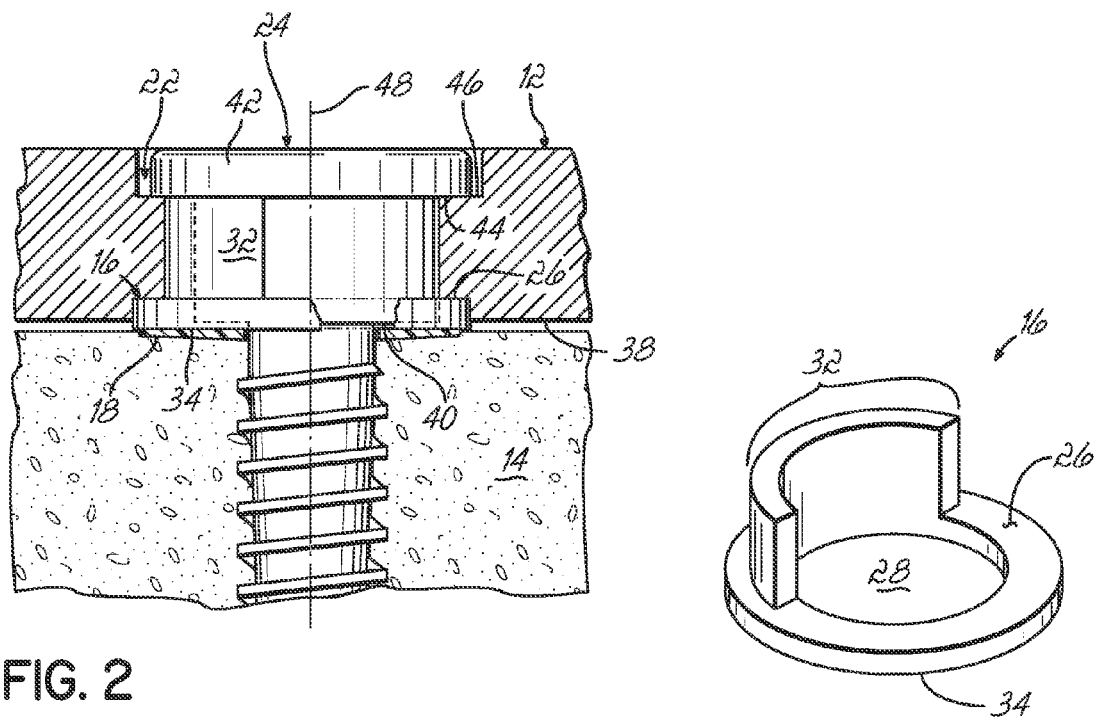
FIG. 2
FIG. 3

SPACER WITH A COATING THEREON FOR USE WITH AN IMPLANT DEVICE

FIELD OF THE INVENTION

The present invention generally relates to a spacer for use with implant devices, e.g., bone plates, and, more specifically, to spacers having a coating thereon, wherein the coating includes a therapeutic healing agent(s) such as to stimulate bone growth and/or promote fracture healing.

BACKGROUND

Implant devices, such as bone plates, can be implanted in the body for the splinting of a fracture at a bone. To that end, the bone plate may be provided with one or more holes and accompanied by one or more securing means, e.g., bone screws, as well as spacer devices. The spacer device, or spacer, can be shaped to fit within the hole in the bone plate and accommodate the screw. The spacer, thus, may be inserted within a corresponding hole of the bone plate, then the screw inserted through both the hole and spacer. The screw may be screwed into bone to fix the bone plate thereto for splinting of a fracture, with the spacer being situated between the bone screw and the bone plate in the direction towards the fracture upon implantation. The spacer, which may be polymeric and elastic in nature, functions to improve bone fracture healing by acting as a cushion between the bone plate and the bone screw and by decreasing the area of contact between bone and the bone plate thereby permitting a restricted displacement in compression stressing of the bone.

It would be desirable to provide an improved spacer for use with an implant device, e.g., a bone plate, which further stimulates bone growth and/or promotes fracture healing.

SUMMARY

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

In an embodiment of the present invention, a device defining a spacer, e.g., a polymeric spacer, is provided for use with an implant device, e.g., a bone plate, for splinting a fracture of a bone. The spacer includes a body defining a bone healing surface, wherein at least a portion of the bone healing surface has a coating thereon which includes a therapeutic agent, a polymeric carrier, and a buffer medium to stimulate bone growth and/or promote fracture healing.

In another embodiment, a kit is provided which includes one or more spacers, at least one bone plate, and optionally one or more bone screws for securing he bone plate to bone. At least one spacer includes a body defining a bone-healing surface. At least a portion of the bone-healing surface includes a coating having a therapeutic agent, a polymeric carrier, and a buffer medium to stimulate bone growth and/or promote fracture healing.

In another embodiment, a method for healing bone is provided which includes securely situating a bone plate adjacent a bone wherein the bone plate includes a spacer having a coating on at least a portion thereof. The coating is in contact with the bone and includes a therapeutic agent, a polymeric carrier, and a buffer medium for healing bone. In one example, the coating is placed on at least the portion of the spacer prior to securely situating the bone plate. In another example, the therapeutic agent, the polymeric carrier, and the buffer medium, which define the coating, are mixed prior to placing the coating on at least the portion.

Concerning the coating, the therapeutic agent can include a drug, a biological factor, or mixtures thereof; the polymeric carrier can include a bioresorbable or water-soluble polymer, a hydrogel-forming polymer, a polyelectrolyte, or mixtures thereof; and the buffer medium can include deionized water, phosphate buffer saline, normal saline, serum, whole blood, or mixtures thereof.

Various features discussed below in relation to one or more of the exemplary embodiments may be incorporated into any of the above-described aspects of the present invention alone or in any combination. Again, the brief summary presented above is intended only to familiarize the reader with certain aspects and contexts of the present invention without limitation to the claimed subject matter.

BRIEF DESCRIPTION OF THE FIGURES

Various features, aspects, and advantages of the present invention will become better understood when the following detailed description is read with reference to the accompanying figures in which like characters represent like parts throughout the figures, wherein:

FIG. 1 is a perspective view of a section of bone plate secured to bone by a first bone screw, and a spacer positioned in a hole of the bone plate receiving a corresponding second bone screw.

FIG. 2 is a cross-sectional view of the bone plate of FIG. 1 taken along line 2-2; and FIG. 3 is a perspective view of the spacer of FIG. 1.

DETAILED DESCRIPTION OF EXEMPLARY EMBODIMENTS

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of the present invention (E.G., the exemplary embodiments(s) thereof), the articles "a", "an", "the" and "said" are intended to mean that there are one or more of the elements. The terms "comprising", "including" and "having" are intended to be inclusive and mean that there may be additional elements other than the listed elements.

FIGS. 1-3 show an embodiment of the present invention including a medical device 10 including an implant device 12, e.g., a bone plate (shown in partial), for splinting a fracture of a bone 14 and a spacer 16, such as a polymeric spacer, with a coating 18 thereon used in combination with the bone plate 12 to stimulate bone growth and/or promote fracture healing.

With reference to FIGS. 1 and 2, the bone plate 12 includes two holes 22 with each 22 hole receiving a corresponding polymeric spacer 16 and a corresponding bone screw 24. The bone plate 12 may be composed of metals and metal alloys, such as titanium or titanium alloys, tantalum or tantalum alloys (e.g., Ti6Al4V or Protosul™), stainless steel or alloys thereof, cobalt-based alloys, cobalt-chromium alloys, cobalt-chromium-molybdenum alloys, niobium alloys, zirconium alloys, as well as shape memory alloys such as NiTiNOL. The bone plate 12 may define, for example, a compression bone plate (e.g. an axially compressive bone plate) or locking bone plate as are known in the art.

The polymeric spacer 16, as best shown in FIG. 3, includes a generally circular-shaped body 26 having an aperture 28 therethrough so as to receive a correspondingly-shaped screw 24 and further includes a protrusion 32 extending generally perpendicularly away from the body 26 to help retain the polymeric spacer 16 within the hole 22, as generally discussed further below. The polymeric spacer 16 functions to improve bone fracture healing by acting as a cushion between the bone plate 12 and bone screw 24 and by decreasing the area of contact between bone 14 and the bone plate 12 thereby permitting a restricted displacement in compression stressing of the bone 14. And, although shown as being generally circular-shaped and having the protrusion 32 therefrom, it should be understood by one having ordinary skill in the art that various spacer 1 6 configurations may be provided for cooperation with differently shaped and sized holes 22 and/or screws 24.

The coating 18 on spacer 16 includes a therapeutic healing agent, a polymeric carrier, and a buffer medium. The coating 18 is applied to a bottom, or bone-healing, surface 34 of the spacer 16, and contacts the bone 14 (or bony tissue) when the bone plate 12 is implanted. Such coating 18 helps mitigate the development of stress shielding and further promotes bone growth and/or fracture healing. One such suitable bone plate 12 (with screws 24) and polymeric spacer 16, which may receive the coating 18 in accordance with an embodiment of the present invention, are disclosed in U.S. Pat. No. 6,540,746 to Buhler et al. entitled "Bone Plate for Splinting a Fracture at a Bone with a Plurality of Bone Screws", which is expressly incorporated by reference herein in its entirety.

As best shown in FIGS. 1 and 2, the bone plate 12 is attached to the bone 14 using each bone screw 24. Prior to positioning the screws 24 within corresponding holes 22, a corresponding polymeric spacer 16 first is positioned in each hole 22. To position the polymeric spacer 16, the polymeric spacer 16 may be pressed into the hole 22 from the underside 38 of the bone plate 12, which lies adjacent to the bone 14 when implanted. The polymeric spacer 16 is held in place within the hole 22 by a snap or friction-type fit and is oriented so that the coating 18 on the polymeric spacer 16 contacts bone 14 when the bone plate 12 is implanted. The bone screws 24 then are inserted through the corresponding hole 22 and spacer 16, and ultimately anchored in the bone 14 and braced thereagainst via contact surface 40. The screw head 42, which is sunk within the bone plate 12, has in its upper region a shoulder 44 that lies in contact with a ring-shaped ledge 46 in the hole 22 of the bone plate 12 and limits the plate's upward movement in the direction of a screw axis 48. The contact surface 40 of the bone screw 24 projects beyond the underside 38 of the bone plate 12, which is at least so large that the underside 38 does not lie in contact with the bone 14. The distance is chosen to be greater than about 0.2 mm in order that the underside 38 of the bone plate 12 reliably lies spaced apart from the bone 14 between the bone screws 24.

The polymeric spacer 16 likewise projects beyond the underside 38 of the bone plate 12 at its bone-healing surface 34 by a distance, which can be smaller than the distance for the contact surface 40 of the screw 24, in order that the bone plate 12 is braced with only a limited force between the polymeric spacer 16 and the shoulder 44. A compression of the bone 14 and a moving back is possible insofar as the polymeric spacer 16 and the friction between the shoulder 44 and the ledge 46, which is produced by the bias force, permit. Because the material for the polymeric spacer 16 may be bioresorbable, the deflections of micro-movements can be controlled temporally in such a manner that pressure peaks, which become ever greater but still remain tractable during backward movement, are permitted at the fracture. The bone 14 can thus take over its carrying function in accordance with the healing process, which has a very positive effect on bone forming.

The polymeric spacer 16, in accordance with embodiments of the present invention, may be composed of a bioresorbable or biostable polymer and includes a desired elasticity. The bioresorbable polymer can include a poly-D, L-lactide (PDLLA), which may be resorbed through hydrolysis in approximately 30 weeks. A suitable PDLLA is Resomer R208 available from the Boehringer Company of Ingelheim, Germany. The bioresorbable polymer can also include poly (L) lactide (PLLA), a copolymer of PLLA and PDLLA, polyglycolide (PGA), and copolymers of PGA and polylactide with different molecular weights (or inherent viscosity). Biostable polymers can include poly(methylmethacrylate), poly(ether ether ketone), ultrahigh molecular weight polyethylene, and polyurethane, for example.

As best shown in FIG. 2, the bottom, or bone-healing, surface 34 of the polymeric spacer 16 is coated with coating 18, which is in contact with the bone 14. That coating 18, as disclosed above, includes a therapeutic healing agent, a polymeric carrier, and a buffer medium. The therapeutic agent is such that it promotes bone growth and/or fracture healing. The coating is applied at a thickness that allows delivery of a desired amount of the therapeutic agent over a desired period of time.

The therapeutic healing agent of the coating 18 can include, for example, a drug or biological factor, such as an osteogenic agent, an osteoinductive agent, or mixture thereof, which can promote bone growth and/or healing, thus, enhancing the overall healing characteristics of the medical device. Such osteogenic and osteoinductive agents can include, for example, members of the families of Bone Morphogenetic Proteins (BMPs), Osteoprotegerin or any of the other osteoclastogenesis inhibitors, Connective Tissue Growth Factors (CTGFs), Vascular Endothelial Growth Factors (VEGFs), Transforming Growth Factor-betas (TGF-βs), Growth Differentiation Factors (GDFs), Cartilage Derived Morphogenic Proteins (CDMPs), and Lim Mineralization Proteins (LMPs). Osteoconductive agents may optionally be provided in the coating 18 along with the osteogenic and/or osteoinductive agents.

BMPs are a class of proteins thought to have osteoinductive or growth-promoting activities on endogenous bone tissue, or function as pro-collagen precursors. Known members of the BMP family that may be utilized as osteoinductive agents in tissue attachment formulations include BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, and BMP-18 polynucleotides and polypeptides, as well as mature polypeptides and polynucleotides encoding the same. The BMPs may be included in the coating 18 as full length BMPs or fragments thereof, or combinations or mixtures thereof, or as polypeptides or polynucleotides encoding the polypeptide fragments of all of the recited BMPs. (Termaat et al., J Bone Joint Surg Am., 87:1367-138, 2005).

Osteoclastogenesis inhibitors inhibit bone resorption by osteoclasts of the bone tissue surrounding the site of implantation. Osteoclast and Osteoclastogenesis inhibitors include osteoprotegerin polynucleotides and polypeptides, as well as mature Osteoprotegerin polypeptides and polynucleotides encoding the same. The Osteoprotegerin protein specifically binds to its ligand, osteoprotegerin ligand (TNFSF11/OPGL), both of which are key extracellular regulators of osteoclast development. Osteoclastogenesis inhibitors further include chemical compounds such as bisphosphonates (e.g., alendronate, clodronate, etidronate, ibandronate, (3-amino-1-hydroxypropylidene)-1,1-bisphosphonate (APD), dichloromethylene bisphosphonate, aminobisphosphonatezolendronate, zoledronic acid, and pamidronate) (Morris et al., J Bone Joint Surf Am., 87: 1609-1618, 2005), 5-lipoxygenase inhibitors such as those described in U.S. Pat. Nos. 5,534,524 and 6,455,541 (herein incorporated by reference), heterocyclic compounds such as those described in U.S. Pat. No. 5,658,935 (herein incorporated by reference), 2,4-dioxoimidazolidine and imidazolidine derivative compounds such as those described in U.S. Pat. No. 5,397,796 and 5,554,594 (herein incorporated by reference), sulfonamide derivatives such as those described in U.S. Pat. No. 6,313,119 (herein incorporated by reference), and acylguanidine compounds such as those described in U.S. Pat. No. 6,492,356 (herein incorporated by reference).

CTGFs are a class of proteins thought to have growth-promoting activities on connective tissues. Known members of the CTGF family include CTGF-1, CTGF-2, and CTGF-4, any of which may be incorporated into the coating 18, in addition to polypeptides and polynucleotides encoding the same.

VEGFs are a class of proteins thought to have growth-promoting activities on vascular tissues. Known members of the VEGF family include VEGF-A, VEGF-B, VEGF-C, VEGF-D and VEGF-E, any of which may be incorporated into the coating 18, in addition to polypeptides and polynucleotides encoding the same.

TGF-βs are a class of proteins thought to have growth-promoting activities on a range of tissues, including connective tissues. Known members of the TGF-β family include TGF-β-1, TGF-β-2, and TGF-β-3, any of which may be incorporated into the coating 18, in addition to polypeptides and polynucleotides encoding the same.

Known GDFs include GDF-1, GDF-2, GDF-3, GDF-7, GDF-10, GDF-11, and GDF-15. GDF-1 polynucleotides and polypeptides generally correspond to GenBank Accession Numbers M62302, AAA58501, and AAB94786; GDF-2 polynucleotides and polypeptides correspond to GenBank Accession Numbers BC069643, BC074921, Q9UK05, AAH69643, and AAH74921; GDF-3 polynucleotides and polypeptides correspond to GenBank Accession Numbers AF263538, BC030959, AAF91389, AAQ89234, and Q9NR23; GDF-7 polynucleotides and polypeptides correspond to GenBank Accession Numbers AB158468, AF522369, AAP97720, and Q7Z4P5; GDF-10 polynucleotides and polypeptides correspond to GenBank Accession Numbers BC028237 and AAH28237; GDF-11 polynucleotides and polypeptides correspond to GenBank Accession Numbers AF100907, NP005802 and O95390; and GDF-15 polynucleotides and polypeptides correspond to GenBank Accession Numbers BC008962, BC000529, AAH00529, and NP004855.

Known CDMPs and LMPs include CDMP-1, CDMP-2, LMP-1, LMP-2, and LMP-3. CDMP-1 polynucleotides and polypeptides generally correspond to GenBank Accession Numbers NM000557, U13660, NP000548 and P43026; CDMP-2 polypeptides correspond to GenBank Accession Numbers and P55106; LMP-1 polynucleotides and polypeptides correspond to GenBank Accession Numbers AF345904 and AAK30567; LMP-2 polynucleotides and polypeptides correspond to GenBank Accession Numbers AF345905 and AAK30568; and LMP-3 polynucleotides and polypeptides correspond to GenBank Accession Numbers AF345906 and AAK30569.

Additional osteoinductive and osteoconductive agents, factors, and compounds such as hydroxyapatite (HA), tricalcium phosphate (TCP), collagen, fibronectin (FN), osteonectin (ON), endothelial cell growth factor (ECGF), cementum attachment extracts (CAE), ketanserin, human growth hormone (HGH), animal growth hormones, parathyroid hormone (PTH) (Aleksyniene and Hvid, Medicina (Kaunas), 40, 842-849, 2004), epidermal growth factor (EGF), interleukin-1 (IL-1), human alpha thrombin, insulin-like growth factor (IGF-1), platelet derived growth factors (PDGF), fibroblast growth factors (FGF, βFGF, etc.), and Wnt proteins, and derivatives thereof also can be included as therapeutic agents.

Other examples of therapeutic healing agents can include glycogen synthase kinase 3 (GSK-3) inhibitors, biocidal/biostatic sugars such as dextran and glucose, vitamins, cartilage fragments, natural extracts, genetically engineered living cells, or otherwise modified living cells, permeation enhancers such as fatty acid esters including laureate, myristate, and stearate monoesters of polyethylene glycol, salts such as strontium salt, fluoride salt, magnesium salt, and sodium salt, bone marrow aspirate, bone marrow concentrate, and mixtures and combinations thereof.

Therapeutic agents that are full-length proteins or fragments may be conjugated to polyethylene glycol (PEG) moieties to increase their half-life in vivo (also known as pegylation). Methods of pegylating polypeptides are well known in the art. In addition, the biological factor(s) may be delivered by gene therapy vectors harboring the polynucleotides encoding the biological factor of interest. The vector may be, for example, a phage, plasmid, viral, or retroviral vector. Such gene therapy and delivery techniques are known in the art. Gene therapy vectors further comprise suitable adenoviral vectors. Suitable gene therapy vectors include gene therapy vectors that do not integrate into the host genome and gene therapy vectors that integrate into the host genome. A desired polynucleotide also may be delivered in plasmid formulations. Plasmid DNA or RNA formulations refer to polynucleotide sequences encoding osteoinductive polypeptides that are free from any delivery vehicle that acts to assist, promote, or facilitate entry into the cell, including viral sequences, viral particles, liposome formulations, lipofectin or precipitating agents and the like.

The biological factors also may be available as heterodimers or homodimers, as well as multimers or combinations thereof. Recombinantly expressed proteins may be in native forms, truncated analogs, muteins, fusion proteins (e.g., fusion proteins with the FC portion of human IgG), and other constructed forms capable of inducing bone, cartilage, or other types of tissue formation as demonstrated by in vitro and ex vivo bioassays and in vivo implantation in mammals, including humans. Examples of fusion proteins include ligand fusions between mature osteoinductive polypeptides and the FC portion of human Immunoglobulin G (IgG). Methods of making fusion proteins and constructs encoding the same are known in the art.

Examples of suitable drugs include antitumor agents and chemotherapeutics such as cis-platinum, ifosfamide, methotrexate, and doxorubicin hydrochloride, immuno-suppressants, statins, pain killers and anti-inflammatories such as non-steroidal anti-inflammatory drugs (NSAID) like ketorolac tromethamine, lidocaine hydrochloride, bipivacaine hydrochloride, and ibuprofen, antibiotics or other bactericidal agents, and antiretroviral drugs. Bactericidal drugs and antiretroviral drugs may be provided to prevent infection by pathogens that are introduced to the patient during implant surgery. Administration of antibiotics and antiretroviral drugs also may be useful to account for nosocomial infections or other factors specific to the location where implant surgery is conducted. Antibiotics and antiretroviral drugs include aminoglycosides such as tobramycin, amoxicillin, ampicillin, azactam, bacitracin, beta-lactamases, beta-lactam(glycopeptide), biomycin, clindamycin, chloramphenicol, chloromycetin, cefazolin, cephalosporins, ciprofloxacin, erythromycin, fluoroquinolones, gentamicin, macrolides, metronidazole, neomycin, penicillins, polymycin B, quinolones, rapamycin, rifampin, streptomycin, sulfonamide, tetracyclines, trimethoprim, trimethoprim-sulfamethoxazole, vancomycin, and mixtures and combinations thereof. Bactericidal agents include the group of metal ions such as silver and copper.

The polymeric carrier of coating 18 generally functions as a delivery medium to allow for regulated and sustained release of the therapeutic agent. The polymeric carrier can include natural or synthetic polymers such as bioresorbable or water-soluble polymers, hydrogel-forming polymers, polyelectrolytes, or mixtures thereof. Examples of suitable bioresorbable or water-soluble polymers include anionic biopolymers such as alginate and hyaluronic acid, cationic biopolymers such as chitin and chitosan, amphipathic polymers such as collagen, gelatin and fibrin, and neutral biopolymers such as dextran and agarose. Examples of suitable hydrogel-forming polymers include polyoxyethylene polyoxypropylene block copolymer (e.g. BASF Lutrol F 127), poly(ethylene glycol)-co-polylactide, poly(ethylene oxide), poly(amino acids), and synthetic polypeptides. Examples of suitable polyelectrolytes include poly(acrylic acid), and poly(acrylic acid) and poly(allyamine hydrochloride) such as to provide multi-layer films (Pavoor et al., Biomaterials, 27, 1527-1533, 2006).

The buffer medium of coating 18 can include, for example, deionized water, phosphate buffer saline, normal saline (e.g., 0.9% weight to volume NaCl solution in deionized water), serum, or whole blood, or mixtures thereof. The buffer medium generally is selected to provide a desirable pH environment for the therapeutic agent. In one embodiment, the buffer medium, in combination with the polymeric carrier, provides a solution for the therapeutic agent having a pH of about 4 to about 9. In another embodiment, the buffer medium/polymeric carrier solution has a pH of about 5 to about 8. In yet another embodiment, the buffer medium/polymeric carrier solution has a pH of about 5.5 to about 7.5.

Concerning the amounts of each component in the coating 18, the therapeutic healing agent, in one embodiment, is provided in a range of about 0.01 mg/mL to about 50 mg/mL, expressed as weight of therapeutic healing agent(s) per volume of polymeric carrier(s). In another embodiment, the therapeutic healing agent is provided in a range of about 0.3 mg/mL to about 10 mg/mL. In yet another embodiment, the therapeutic healing agent is provided in a range of about 0.5 mg/mL to about 5 mg/mL.

The polymeric carrier, in one embodiment, is provided in the coating 18 in a range of about 1% to about 90% weight per volume of buffer medium. In another embodiment, the polymeric carrier is provided in a range of about 5% to about 50% weight per volume of buffer medium. In yet another embodiment, the polymeric carrier is provided in a range of about 10% to about 30% weight per volume of buffer medium.

In one example, the coating 18 of the present invention includes a growth factor, a hydrogel-forming polymer, and a buffer medium. In another example, the coating 18 includes bone morphogenetic protein (BMP), a polyoxyethylene polyoxypropylene block copolymer, and deionized water. In yet another example, the coating 18 includes 1.5 mg/mL recombinant human bone morphogenetic protein 2 (rhBMP-2) and 20% wt/vol polyoxyethylene polyoxypropylene block copolymer (i.e., BASF Lutrol® F 127) in deionized water.

The coating 18 may be coated onto the bone-healing surface 34 of the spacer 16 at a thickness of about 10 nm to about 1000 μm. In another embodiment, the coating 18 is coated onto the bone-healing surface 34 at a thickness of about 100 nm to about 500 μm. In yet another embodiment, the coating 18 is coated onto the bone-healing surface 34 at a thickness of about 300 nm to about 300 μm. While the bone-healing surface 34 of the spacer 16 is shown as being coated, it should be understood that other areas or portions of the spacer 16 may be coated either alternately or in addition thereto and that less than or more than the entire bone-healing surface 34 may coated. Generally speaking, a surface (or portion) of the spacer 16 that would normally contact bone 14 (or bony tissue), but for the coating 18, typically is coated so as to maximize promotion of bone growth and/or fracture healing.

The coating 18 can be prepared by generally mixing together the respective components and, more specifically, can include first preparing and weighing each of the therapeutic agent, polymeric carrier, and buffer medium. The therapeutic agent then may be added to the buffer medium and the solution mixed until homogenous. The mixing can be done by mechanical stirring, magnetic stirring, or ultrasonically. The polymeric carrier can be added to the homogenous solution then mixed by mechanical stirring, magnetic stirring, or ultrasonically until a homogenous solution is again achieved. The resulting homogenous solution defines the coating 18. During mixing steps, the solution may be subject to an elevated temperature of about 25° C. to about 80° C. In another example, the temperature is within a range of about 30° C. to about 60° C. In another example, the temperature is within a range of about 37° C. to about 45° C. The mixing process typically is carried out in a USP clean room (e.g., 10,000 or higher).

Once mixed, the coating 18 may be sealed and packaged for sterilization for later coating, e.g., dip coating, of the spacer 16, such as in an operating room. Alternatively, the just prepared coating 18 may be subsequently applied to the spacer 16 such as to the bone healing surface(s) 34 thereof. Then, the spacer(s) 16 can be packaged alone or as a kit with the bone plate(s) 12 and corresponding bone screw(s) 24, which may be sterilized such as via a gas plasma process. In another embodiment, rather than the coating 18 being premixed or the spacers 16 pre-coated, each component of the coating 18 may be provided separately weighed and packaged for a surgeon. Prior to surgery, the components, i.e., therapeutic agent, polymeric carrier, and buffer medium can be mixed together, as described above, then the coating can be applied, such as via dip coating 18, onto the surface(s) 34 of the spacer 16 that will be in contact with bone 14 (or bony tissue).

Dip coating of the spacer 16 may be performed in such a way that the surface 34 that would be in contact with the bone 14 (or bony tissues), but for the coating 18, is immersed in the coating 18. Alternately, the entire spacer 16 may be dip coated. In one embodiment, the spacer 16 (or portion thereof) can be immersed in the coating 18 for about 5 seconds to about 300 seconds. In another embodiment, the spacer 16 (or portion thereof) can be immersed in the coating 18 for about 10 seconds to about 180 seconds. In yet another embodiment, the spacer 16 (or portion thereof) can be immersed in the coating 18 for about 30 seconds to about 120 seconds. After immersion, the coating 18 is allowed to dry, e.g., air dry.

Multiple coatings 18 may be applied on the spacer 16. Subsequent coatings may include one or more different components. That different component, for example, may be different in chemistry and/or molecular weight. In one example, the subsequent coating(s) may define, for example, a different drug(s) with the same or different release profile, which may be required to act synergistically in the fracture-healing pathway. Multilayer coatings can modify the profiles of bone resorption and the therapeutic agents release to achieve desirable clinical results.

As various changes could be made in the above-described aspects and exemplary embodiments without departing from the scope of the invention, it is intended that all matter contained in the above description shall be interpreted as illustrative and not in a limiting sense.

What is claimed is:

1. A method for healing bone comprising:
   situating a bone plate adjacent a bone, the bone plate having at least one aperture;
   inserting at least one spacer into the at least one aperture of the bone plate to space the bone plate from the bone and decrease the area of contact between the bone and the bone plate, wherein the spacer includes a bone healing surface that projects beyond an underside surface of the bone plate, wherein the spacer is bioresorbable and includes a coating on at least a portion of the bone healing surface, and wherein the coating is in contact with the bone and comprises effective amounts of a therapeutic agent, a polymeric carrier and a buffer medium; and
   securing the bone plate to the bone.

2. The method of claim 1 further including prior to situating the bone plate, placing the coating on at least the portion of the at least one spacer.

3. The method of claim 2 further comprising prior to placing the coating on at least the portion of the at least one spacer, mixing the therapeutic agent, the polymeric carrier, and the buffer medium to define the coating.

4. The method of claim 1 wherein the therapeutic agent includes a drug, a biological factor, or mixtures thereof.

5. The method of claim 1 wherein the therapeutic agent includes an osteogenic agent, an osteoinductive agent, or mixtures thereof.

6. The method of claim 1 wherein the therapeutic agent is a bone growth factor.

7. The method of claim 6 wherein the bone growth factor is a bone morphogenetic protein.

8. The method of claim 1 wherein the polymeric carrier includes a bioresorbable or water-soluble polymer, a hydrogel-forming polymer, a polyelectrolyte, or mixtures thereof.

9. The method of claim 1 wherein the buffer medium includes deionized water, phosphate buffered saline, normal saline, serum, whole blood, or mixtures thereof.

10. The method of claim 1 wherein the therapeutic agent includes a growth factor, the polymeric carrier includes a hydrogel-forming polymer, and the buffer medium includes deionized water.

11. The method of claim 10 wherein the growth factor is recombinant human bone morphogenetic protein 2 (rhBMP-2), and the hydrogel-forming polymer is a polyoxyethylene polyoxypropylene block copolymer.

12. The method of claim 1 wherein a therapeutic healing agent is provided in the coating in a range of about 0.01 mg/mL to about 50 mg/mL, expressed as weight of therapeutic healing agent per volume of polymeric carrier, and wherein the polymeric carrier is provided in the coating in a range of about 1% to about 90% weight per volume of buffer medium.

13. The method of claim 1 wherein the at least one spacer is a polymeric spacer.

14. The method of claim 1 wherein the at least one spacer includes an aperture, the method comprising securing the at least one spacer to the bone plate.

15. The method of claim 14 comprising securing the bone plate to the bone by introducing a bone screw into the bone through the bone plate and spacer apertures.

16. The method of claim 1 wherein the bone plate includes a plurality of apertures, the method comprising inserting a spacer into each of the plurality of apertures.

17. The method of claim 1 comprising securing the at least one spacer into the at least one aperture by snap-fitting said spacer within the aperture.

* * * * *